(12) United States Patent
Rantala et al.

(10) Patent No.: US 7,328,062 B2
(45) Date of Patent: Feb. 5, 2008

(54) MONITORING OF PATIENT'S ELECTRICAL CHARACTERISTICS USING A SINGLE PIECE OF EQUIPMENT

(75) Inventors: Börje Rantala, Helsinki (FI); Juha Virtanen, Helsinki (FI)

(73) Assignee: GE Healthcare Finland Oy, Helinski (FI)

( * ) Notice: Subject to any disclaimer, the term of this patent is extended or adjusted under 35 U.S.C. 154(b) by 583 days.

(21) Appl. No.: 10/070,707

(22) PCT Filed: Jul. 12, 2001

(86) PCT No.: PCT/FI01/00666

§ 371 (c)(1),
(2), (4) Date: Jul. 10, 2002

(87) PCT Pub. No.: WO02/03861

PCT Pub. Date: Jan. 17, 2002

(65) Prior Publication Data

US 2002/0183634 A1     Dec. 5, 2002

(30) Foreign Application Priority Data

Jul. 12, 2000   (FI) .................................. 20001656

(51) Int. Cl.
*A61B 5/0428*   (2006.01)
(52) U.S. Cl. ...................... 600/513; 600/522; 600/544; 600/547
(58) Field of Classification Search ................ 600/300, 600/301, 509, 513, 522, 544, 546, 547
See application file for complete search history.

(56) References Cited

U.S. PATENT DOCUMENTS

| 4,495,950 | A |   | 1/1985 | Schneider |
| 4,577,639 | A | * | 3/1986 | Simon et al. ................ 600/522 |
| 4,825,874 | A | * | 5/1989 | Uhlemann ................... 600/523 |
| 5,002,064 | A | * | 3/1991 | Allain et al. ................. 600/523 |
| 5,029,590 | A |   | 7/1991 | Allain et al. |
| 5,197,479 | A | * | 3/1993 | Hubelbank et al. ......... 600/508 |
| 5,231,990 | A | * | 8/1993 | Gauglitz ..................... 600/510 |
| 5,287,859 | A | * | 2/1994 | John .......................... 600/544 |
| 5,623,925 | A | * | 4/1997 | Swenson et al. ............ 600/301 |
| 5,788,644 | A | * | 8/1998 | Donehoo et al. ........... 600/509 |

(Continued)

FOREIGN PATENT DOCUMENTS

WO    97/49077    12/1997
WO    99/45841    9/1999

OTHER PUBLICATIONS

Patent Abstracts of Japan, JP 57-008418 (Ricoh Elemex Co., julk. Jan. 16, 1982).

(Continued)

*Primary Examiner*—Kennedy J. Schaetzle
(74) *Attorney, Agent, or Firm*—Andrus, Sceales, Starke & Sawall, LLP (57) ABSTRACT

The invention relates to a method and a system for a medical monitoring system, in which method the functions of a patient are measured, and the change in the electric activity of the patient are observed. In the method, the electrocardiogram (EKG), electroencephalogram (EEG), and the impedance cardiograph signal (IKG) are being measured with one piece of measuring equipment.

10 Claims, 8 Drawing Sheets

U.S. PATENT DOCUMENTS 5,931,791 A * 8/1999 Saltzstein et al. ........... 600/513
6,409,684 B1 * 6/2002 Wilk .......................... 600/586
6,796,941 B2 * 9/2004 Williams et al. ............ 600/301

OTHER PUBLICATIONS

Derwent Abstract, 1996-151077, Record Apparatus EEG ECG Simultaneous Display Waveform CRT Computer Compare EEG Signal Obtain Electrode Normal Man Display Result Polygonal Line Graph (Sato).

A Primer for EEG Signal Processing in Anesthesia, Ira J. Rampil, M.S., M.D., Anesthesiology, vol. 89, No. 4, Oct. 1998, pp. 980-1002.

Impedance and Inductance Monitoring of Cardiac Output, Principles and Practice of Intensive Care Monitoring, Martin J. Tobin, McCraw-Hill 1998, ISBN: 007-0650942, pp. 915-921.

* cited by examiner

Prior Art

Fig. 1

Prior Art

MONITORING OF PATIENT'S ELECTRICAL CHARACTERISTICS USING A SINGLE PIECE OF EQUIPMENT

CROSS REFERENCE TO RELATED APPLICATION

The present application is the U.S. national stage application of International Application PCT/FI01/00666, filed Jul. 12, 2001, which international application was published on Jan. 17, 2002 as International Publication WO 02/03861. The International Application claims priority of Finnish Patent Application 20001656, filed Jul. 12, 2000.

The invention relates to medical monitoring systems. In particular, the invention relates to the method as defined in the claims.

FIELD OF THE TECHNIQUE

Methods for monitoring the electric activity of a patient are becoming common. Previously known is a method for measuring the electrocardiogram (EKG). In the measurement, electrodes are attached to the patient, and a small high-frequency current is conducted into them. By measuring the change in the voltage of the electrodes it is possible to observe the electric activity of the patient, and e.g. the muscle activity.

Figure 1:
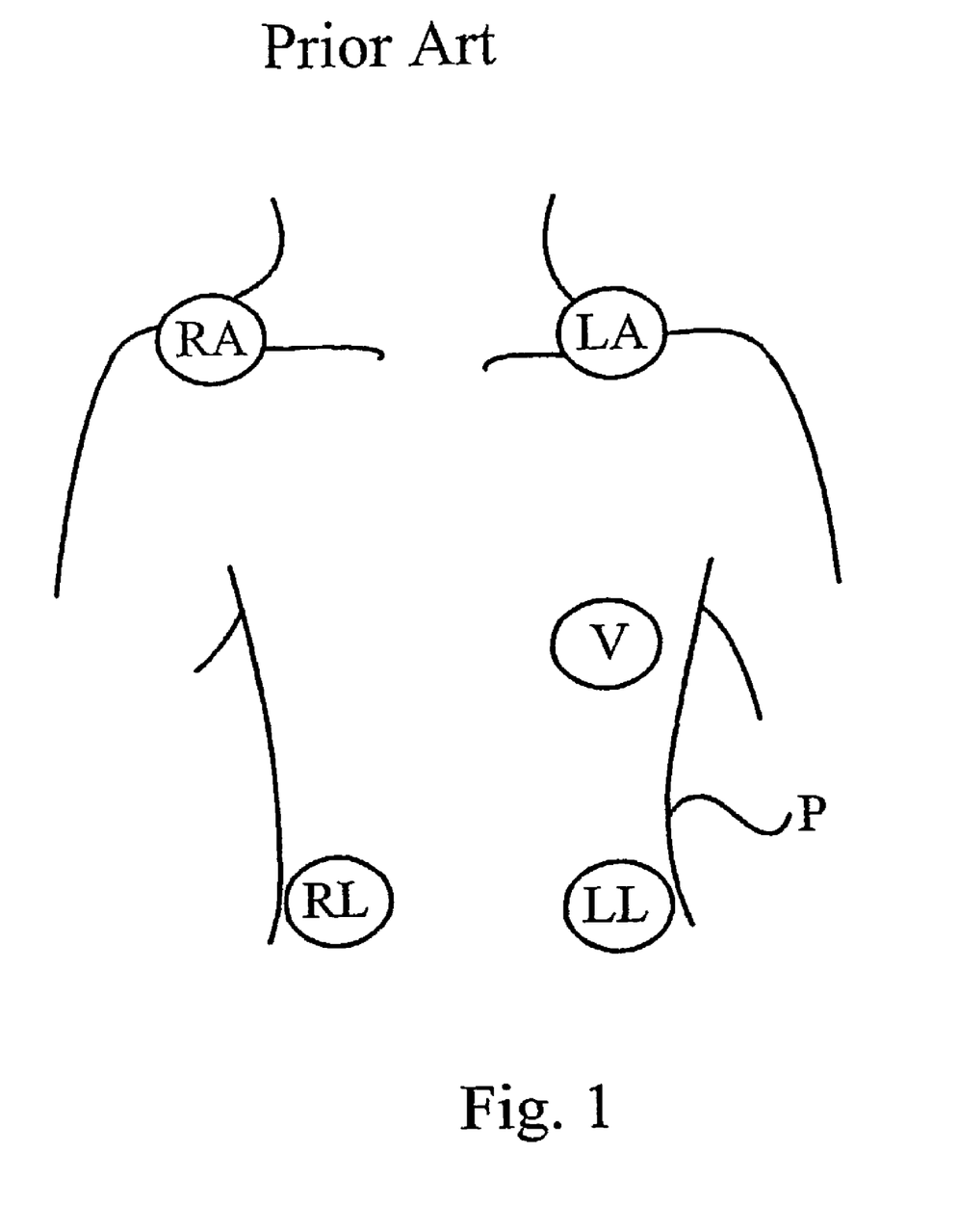
FIG. 1 represents a prior-art placement of electrodes.
Figure 2:
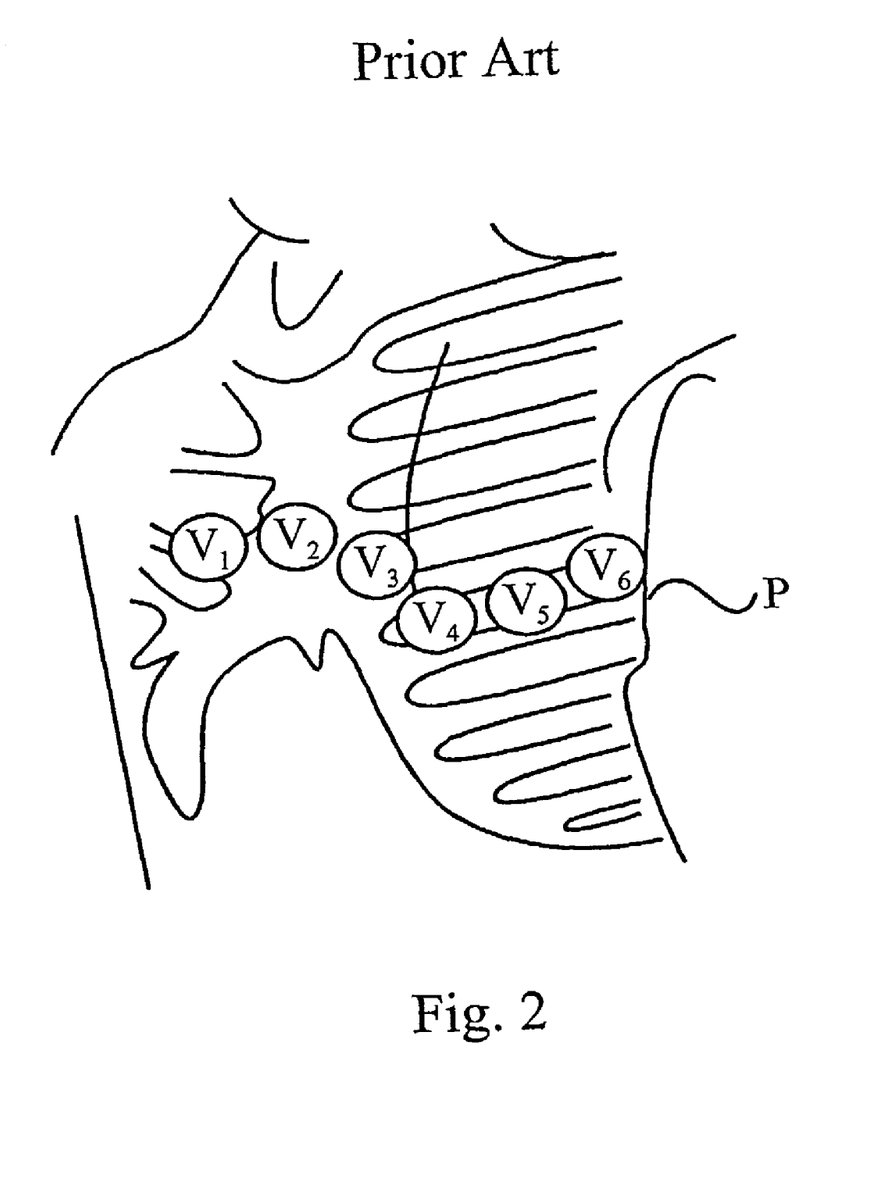
FIG. 2 represents a prior-art placement of electrodes.

Previously known is a system for EKG monitoring as schematically represented in FIGS. 1 and 2. In both figures, two pictures of a torso schematically represent the same patient P, the first of which shows a standard placement of the measuring electrodes PA, LA, RL, and LL (so-called limb leads) for a 5-lead EKG and impedance respiration measurement. For the sake of clarity, the latter figure shows the standard placement of the electrodes $V_1$, $V_2$, $V_3$, $V_4$, $V_5$, $V_6$ of the EKG measurement on the patient's chest as being separate. Together the RA, LA, RL, LL and $V_1$, $V_2$, $V_3$, $V_4$, $V_5$, $V_6$ form a so-called 12-switched switching system. The 5-switched switching system also used in the EKG measuring consists of the electrodes RA, LA, RL, LL, and $V_5$.

The 12-switched system as shown in FIGS. 1 and 2 comprises signal conductors which are connected, according to the standard placement of electrodes, to the corresponding aforementioned measuring electrodes RA, LA, RL, LL, $V_1$, $V_2$, $V_3$, $V_4$, $V_5$, $V_6$ attached to the patient P. Each signal conductor comprises a connector apparatus. The signal conductors are further connected to the EKG equipment making the measurement.

The EKG monitoring and the diagnostic, so-called 12-switched (10-lead) EKG, has been traditionally carried out with separate equipment so that the monitoring took place with a 3- and 5-lead equipment constantly, and the 12-switched usually under the supervision of a cardiologist as a separate event, if necessary.

In the electrocardiogram, and especially in the electroencephalogram (EEG), it is important to monitor the impedance of the electrodes attached to the patient in order to ensure a good quality of the signal. Usually this happens by conducting a small high-frequency current (20-200 kHz) into the electrodes, and by measuring the voltage. In addition, it is common to monitor the respiratory movements of the patient's chest by measuring the small changes in the impedance of the chest. The impedance measurement is also a known method in the estimation of the stroke volume of the heart or changes in it. The principles of the impedance cardiography method have been presented e.g. in the book *"Principles and Practice of Intensive Care Monitoring"*, Martin J. Tobin, McCraw-Hill 1998, ISBN:007-0650942, pages 915-921, to which reference is made herein.

The advantage with the impedance measurement is its simplicity, and that the stroke volume of the heart can be measured continuously and rapidly non-invasively. The disadvantage with the measurement is, however, its inaccuracy, which is due to the correction factors used in empirical formulas which are based on defaults. For example, the weight of the patient, position, the placement of the electrodes, and other corresponding factors have effect on the measurement result. The impedance cardiography is very sensitive to the concentration of fluid of the human body, fatness, and position.

It is possible to utilize the EEG in anesthesia. Then, by observing the diagram produced by the EEG it is possible to ensure the level of anesthesia of the patient. There is a short preamble of the above-mentioned technique presented in the article "A Primer for EEG Signal Processing in Anesthesia", Ira J. Rapil, American Society of Anesthesiologists Inc. 1998, pages 980-1002, to which reference is made herein.

One specific problem is performing measurements e.g. in a small operating room. The prior-art measuring equipment only makes one measurement each. In that case, several devices are needed to make the measurements, in which case the operating room gets filled up with expensive measuring equipment very soon.

Previously known is a solution in which the measurements of the electric activity of a patient are made by a separate device each. The disadvantage with the solution is that in order to make several measurements, several devices are needed. The devices cannot share the conductor connections either, so each device shall have its own conductors and electrodes. On the other hand it is possible to change the conductors and electrodes between the measurement devices, but this is often complicated in an urgent operation.

OBJECTIVE OF THE INVENTION

The objective of the present invention is to eliminate or at least to alleviate the problems referred to above. One further objective of the invention is to enable two or three measurements with one piece of electronic equipment. In that case there are cost savings resulting when there is a smaller number of expensive measuring devices needed in the operating room. The invention also enables one to save space in the operating room, since only one piece of equipment is needed for making the measurements. In a narrow operating room full of instruments the saving of space is a remarkable improvement.

SUMMARY OF THE INVENTION

The invention enables one to make measurements of the electric activity of a patient with one piece of equipment. The equipment comprises ten signal conductors which are used together in different measurements in the same equipment.

The invention relates to a method for a medical monitoring system. In the method, the functions of a patient are measured, and the changes in the electric activity of the patient are observed. In particular, in the invention, the electric activity of a patient is measured, and an electrocardiogram (EKG), electroencephalogram (EEG), and a signal (IKG) from an impedance cardiograph are taken with one piece of equipment.

In one embodiment of the invention, ten conductors are used for the observation and measuring of the patient's electrocardiogram (EKG), electroencephalogram (EEG), and impedance cardiograph signal (IKG). By means of the conductor configuration it is possible to select the measurement to be made. On the other hand the measurement to be made may be selected by a switch. In one embodiment of the invention, when measuring the electrocardiogram (EKG) the selector switch is turned into a first position. In one embodiment of the invention, when measuring the electroencephalogram (EEG) the selector switch is turned into a second position. In one embodiment of the invention, when measuring the impedance cardiograph signal (IKG) the selector switch is turned into a third position.

In one embodiment of the invention, the channels transferring the electroencephalogram (EEG) are changed to a bigger resistance by means of a control device.

In one embodiment of the invention, the electric activity of the muscles in the facial region are being monitored (EMG).

In one embodiment of the invention, from the observed signals, an index describing the depth of the anesthesia is calculated. This enables one to make sure of the quality of the anesthesia during the operation.

In one embodiment of the invention, the electroencephalogram channels (EEG) use the same neutral electrode with the electrocardiogram channels (EKG).

In one embodiment of the invention, based on the impedance relations of the electrodes, the configuration of the electrodes is estimated, in which case it is possible to judge what measurements are supposed to be made.

In one embodiment of the invention, from a 5-lead electrocardiogram (EKG), a 3-lead electrocardiogram (EKG) and a 2-lead electroencephalogram (EEG) are derived.

In one embodiment of the invention, the medical monitoring system of the invention comprises signal conductors, which are connected to the measuring electrodes attached to the patient according to the standard placement of electrodes, and which each signal conductor comprises a first connector apparatus; and measuring equipment which comprises electrocardiogram (EKG), electroencephalogram (EEG), and impedance cardiograph signal equipment (IKG). According to the invention, the equipment comprises a selector switch for selecting the measurement type so that in the first position of the switch, the signal conductors are connected to the 12 lead electrocardiogram equipment (EKG), in the second position of the switch, the signal conductors are connected to the electroencephalogram equipment (EEG), and in the third position of the switch, the signal conductors are connected to the impedance cardiograph signal equipment (IKG).

In one embodiment of the invention, the system comprises a preamplifier unit which may be used to monitor the 12-switched electrocardiogram (EKG), or the limb or full-length impedance cardiograph signal (IKG) of the 5-lead electrocardiogram (EKG) so that the amplifier channels of the chest wiring of the 12-lead electrocardiogram (EKG) transfer to monitor the limb or full-length impedance cardiograph signal (IKG).

In one embodiment of the invention, the system comprises a preamplifier unit and the configuration of the electrodes is estimated based on the impedance relations of the electrodes.

As compared to prior art, the present invention has the advantage that several measurements may be made without having to change the preamplifier or even the signal conductors. The invention also enables one to save space in a narrow operating room, since only one piece of equipment is needed. There are also cost savings resulting, since shared measuring equipment is more advantageous than separate pieces of measuring equipment. Further, the possibility of making several measurements with one piece of equipment lowers the threshold to use the measurements.

LIST OF DRAWINGS

In the following section, the invention will be described by the aid of a few examples of its embodiments with reference to the accompanying drawing, in which.

DETAILED DESCRIPTION OF THE INVENTION

Figure 3:
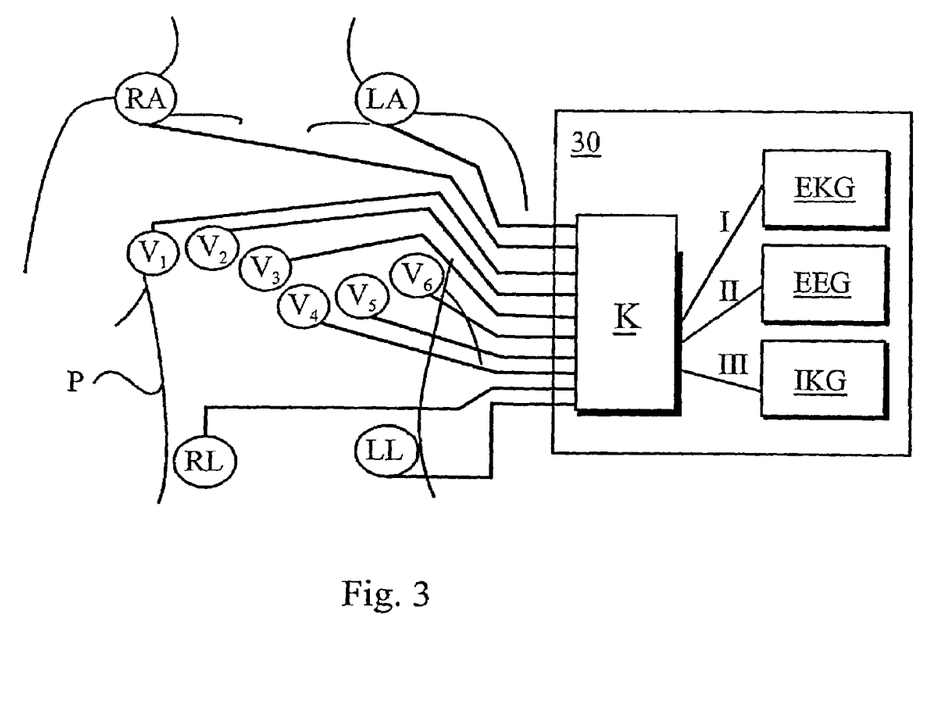
FIG. 3 represents an illustration of the system in accordance with the invention.

FIG. 3 represents one embodiment of the system according to the invention. The measuring electrodes RA, LA, RL, LL, $V_1$, $V_2$, $V_3$, $V_4$, $V_5$, $V_6$ placed on the patient P are connected to the switch K. The switch K is further connected by a first connection I to the measuring equipment of the electrocardiogram EKG, by a second connection II to the measuring equipment EEG of the electroencephalogram, and by a third connection III to the measuring equipment IKG of the impedance cardiograph signal. The switch K may be used to select what measurement is used. The switch K and the pieces of measuring equipment EKG, EEG, and IKG form one piece of integrated measuring equipment 30.

Figure 4:
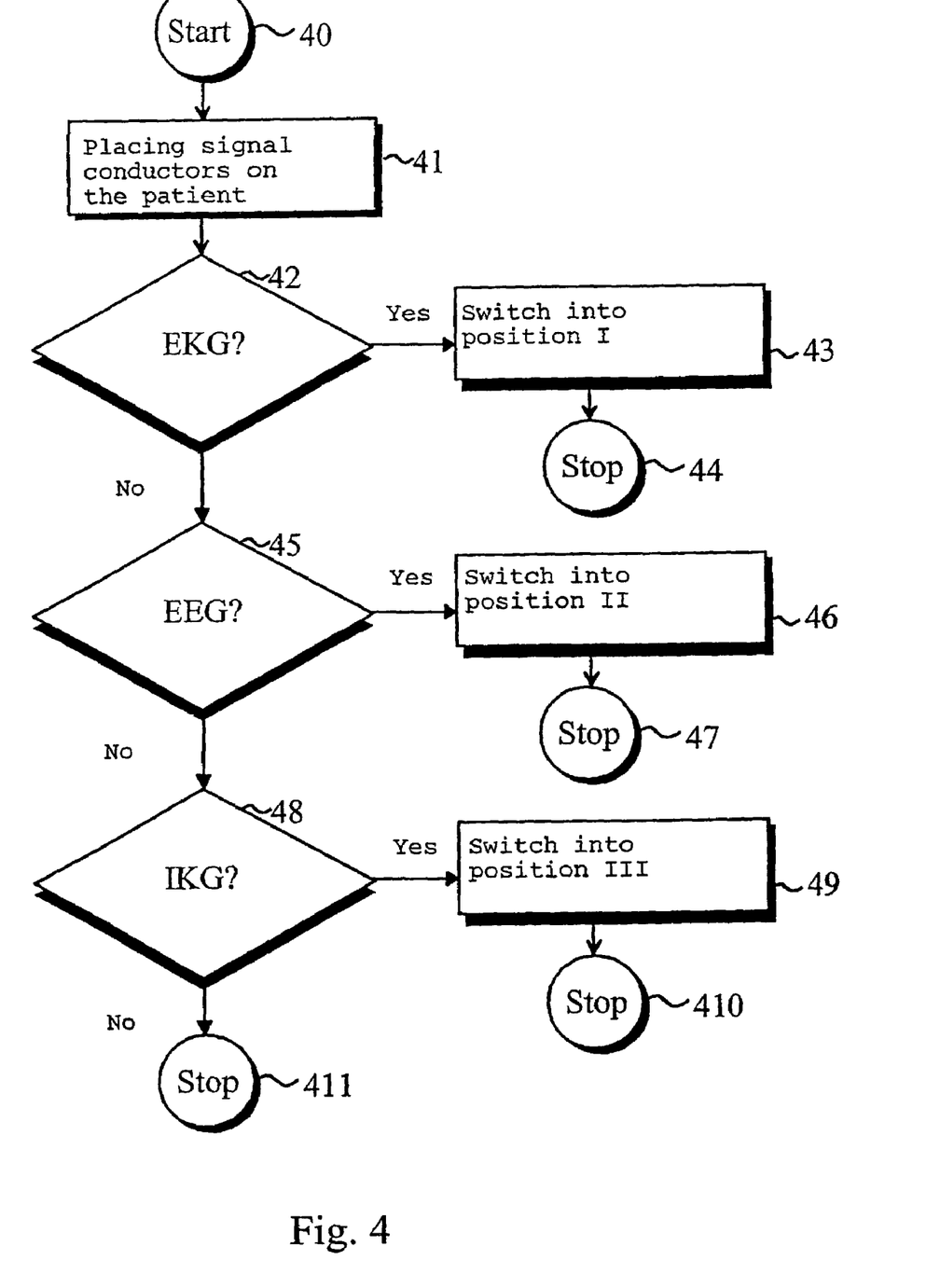
FIG. 4 represents a flow chart illustrating the method of the invention.

FIG. 4 represents a diagram illustrating the method of the invention. At first in the method, the measuring electrodes are placed on the patient. After this, the desired measurement is selected by a switch. If one wishes to measure the EKG, then the switch is turned into position I, points 42 and 43. If EEG is wished to be measured, then the switch K is turned into position II, points 45 and 46. If IKG is wished to be measured, then the switch K is turned into position III, points 48 and 49.

Figure 5:
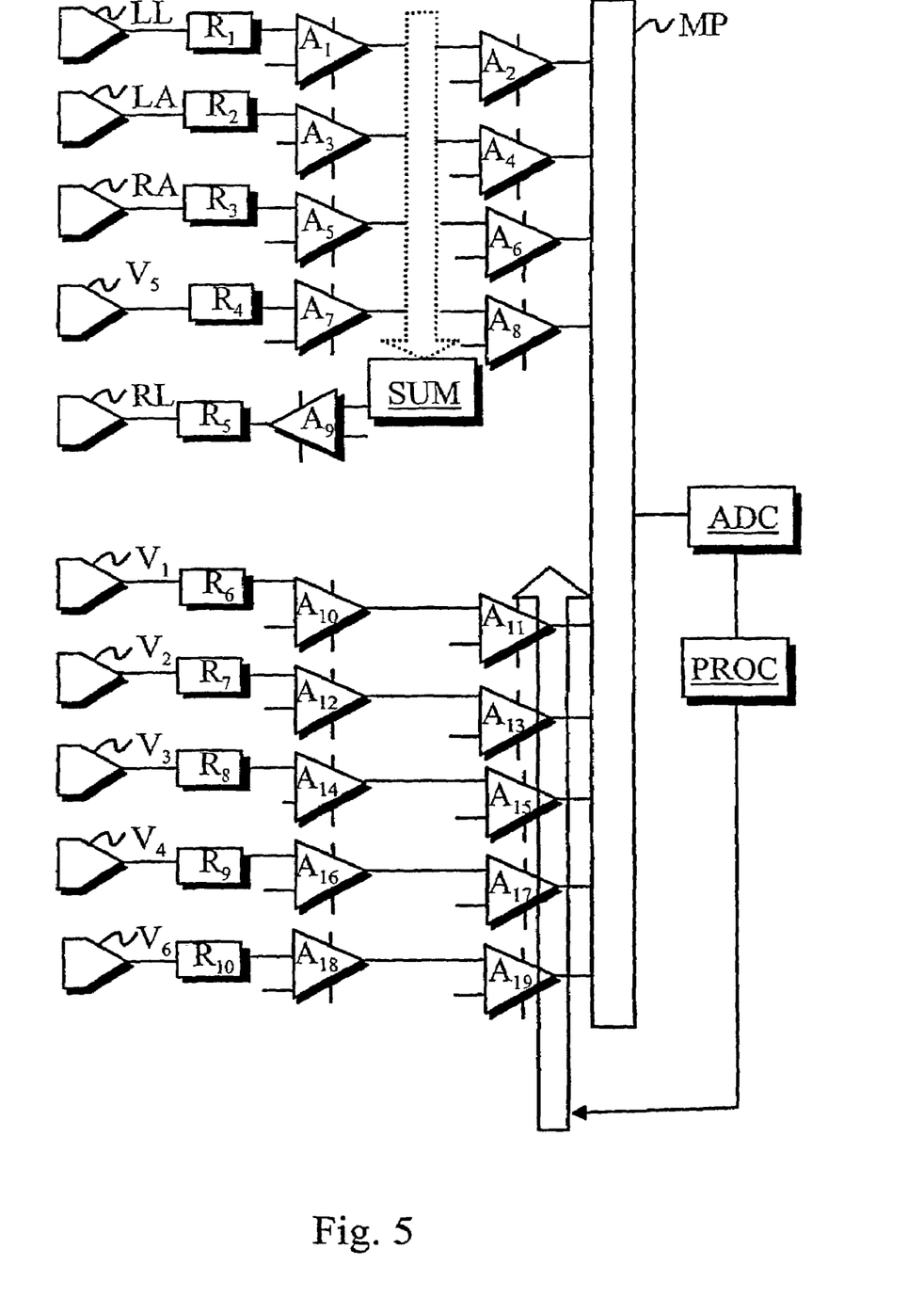
FIG. 5 represents a circuit diagram of the invention.

FIG. 5 represents a circuit diagram in accordance with the invention. The figure shows the measuring of a 12-switched EKG and EEG. The measuring electrodes RA, LA, RI, LL, $V_5$ needed in the measuring of a 5-switched EKG are connected via protective resistors $R_{1\ldots 5}$ to amplifiers $A_{1, 3, 5, 7, 9}$. The signal is further amplified by a second row of amplifiers $A_{2, 4, 6, 8}$, from which there is a connection to a multiplexer MP. Further, from the four measuring electrodes RA, LA, RL, LL, a sum function SUM is calculated. From the multiplexer MP there is a connection via an analog-to-digital converter to a micro-processor PROC. Besides the aforementioned measuring electrodes, for the measuring of a 12-switched EKG and EEG, the measuring electrodes $V_1$, $V_2$, $V_3$, $V_4$, $V_6$ are needed that are connected via the protective resistor $R_{6\ldots 10}$ to the amplifier $A_{10, 12, 14, 16, 18}$. The signal is further amplified by a second row of amplifiers $A_{11, 13, 15, 17, 19}$, from which there is a connection to the multiplexer MP. From the multiplexer MP there is a connection via the analog-to-digital converter to the microprocessor PROC.

Figure 6:
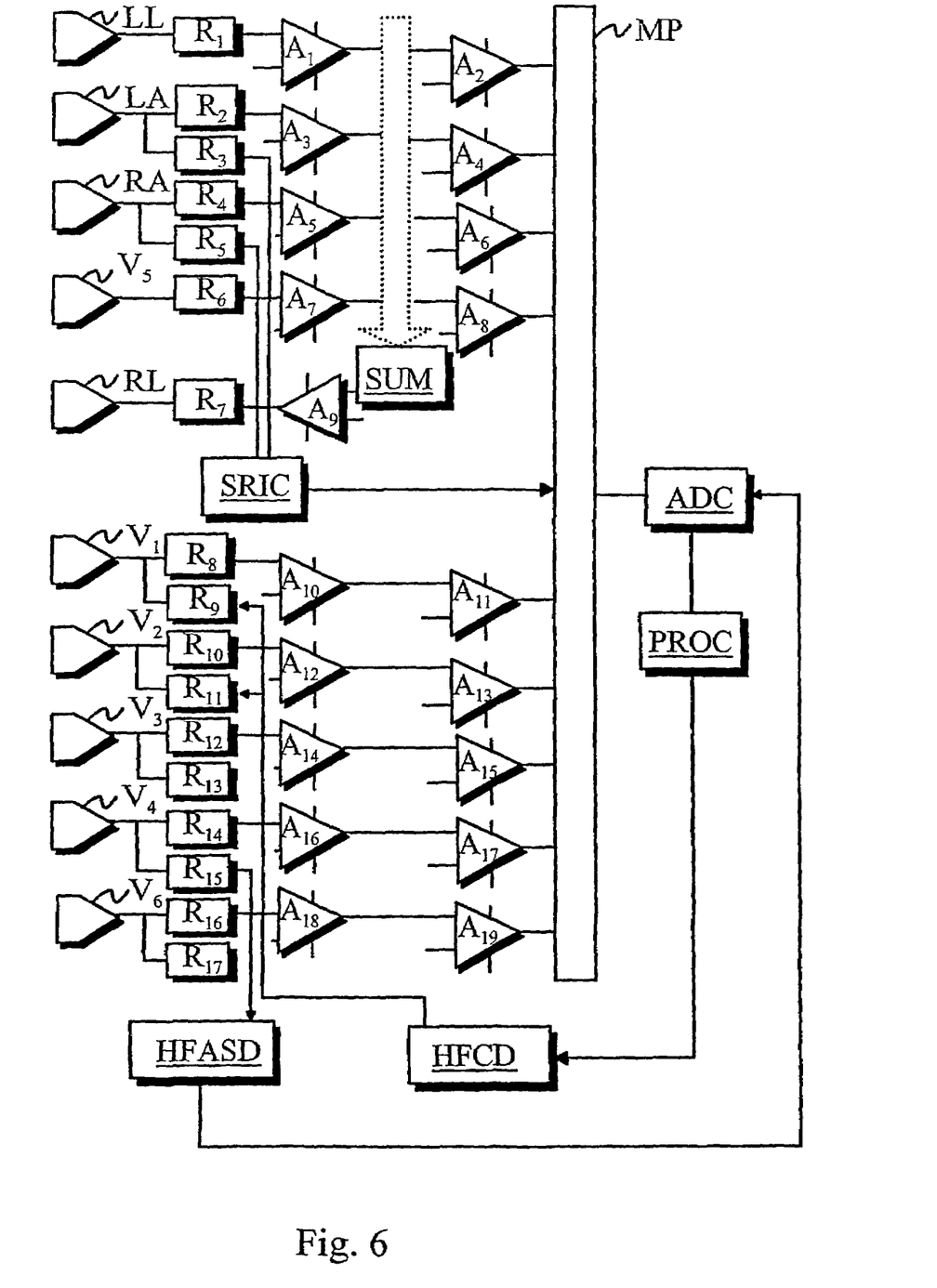
FIG. 6 represents a circuit diagram of the invention.

FIG. 6 represents a circuit diagram in accordance with the invention. The figure shows the measuring of a 12-switched EKG and IKG. For the measuring of a 5-switched EKG, the measuring electrodes RA, LA, RI, LL and $V_5$ on the left-hand corner of the figure are needed are connected via protective resistors $R_{1, 2, 4, 6, 7}$ to amplifiers $A_{1, 3, 5, 7}$. The signal is further amplified by a second row of amplifiers $A_{2, 4, 6, 8}$, which are further connected to the multiplexer MP. From the two measuring electrodes RA and LA there is a connection via protective resistors $R_{3, 5}$ to the standardized measuring circuit SRIC measuring the impedance of breathing, and which is further connected to the multiplexer MP. The multiplexer MP is further connected via an analog-to-digital converter ADC to the micro processor PROC. Besides the aforementioned measuring electrodes, for the measuring of a 12-switched EKG or IKG, the measuring electrodes $V_1$, $V_2$, $V_3$, $V_4$, $V_6$ are needed that are connected via protective resistors $R_{8, 10, 12, 14, 16}$ to amplifiers $A_{10, 12, 14, 16, 18}$ that are further connected to the multiplexer MP. From the multiplexer MP there is a connection via the analog-to-digital converter ADC to the micro-processor PROC. The micro-processor PROC is connected to high-frequency current drivers HFCD from which there is a further a connection to the measuring electrodes $V_1$ and $V_2$ via the protective resistors $R_{9, 11}$. The measuring electrode $V_4$ is connected via the protective resistor $R_{15}$ to the high-frequency amplifiers and to the observation circuit of the synchrone, from which there is a connection via the analog-to-digital transformer ADC to the microprocessor PROC.

Figure 7:
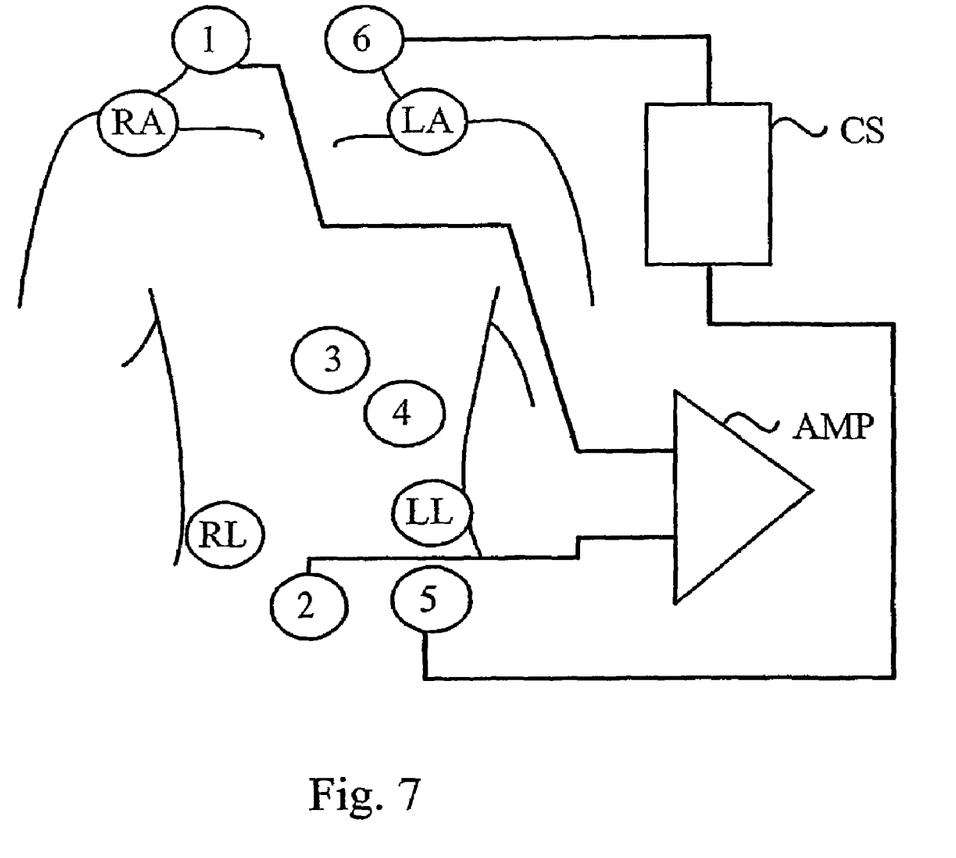
FIG. 7 represents a placement of the electrodes and conductors in accordance with the invention.

FIG. 7 represents one placement of electrodes and conductors in accordance with the invention. The switching of the figure may be used for the observation of a 5-switched EKG. Connected to the amplifier AMP are the measuring electrodes $V_1$ and $V_2$. Further, to a high-frequency current source CS (20-1000 kHz) there are connected the measuring electrodes $V_6$ and $V_5$.

Figure 8:
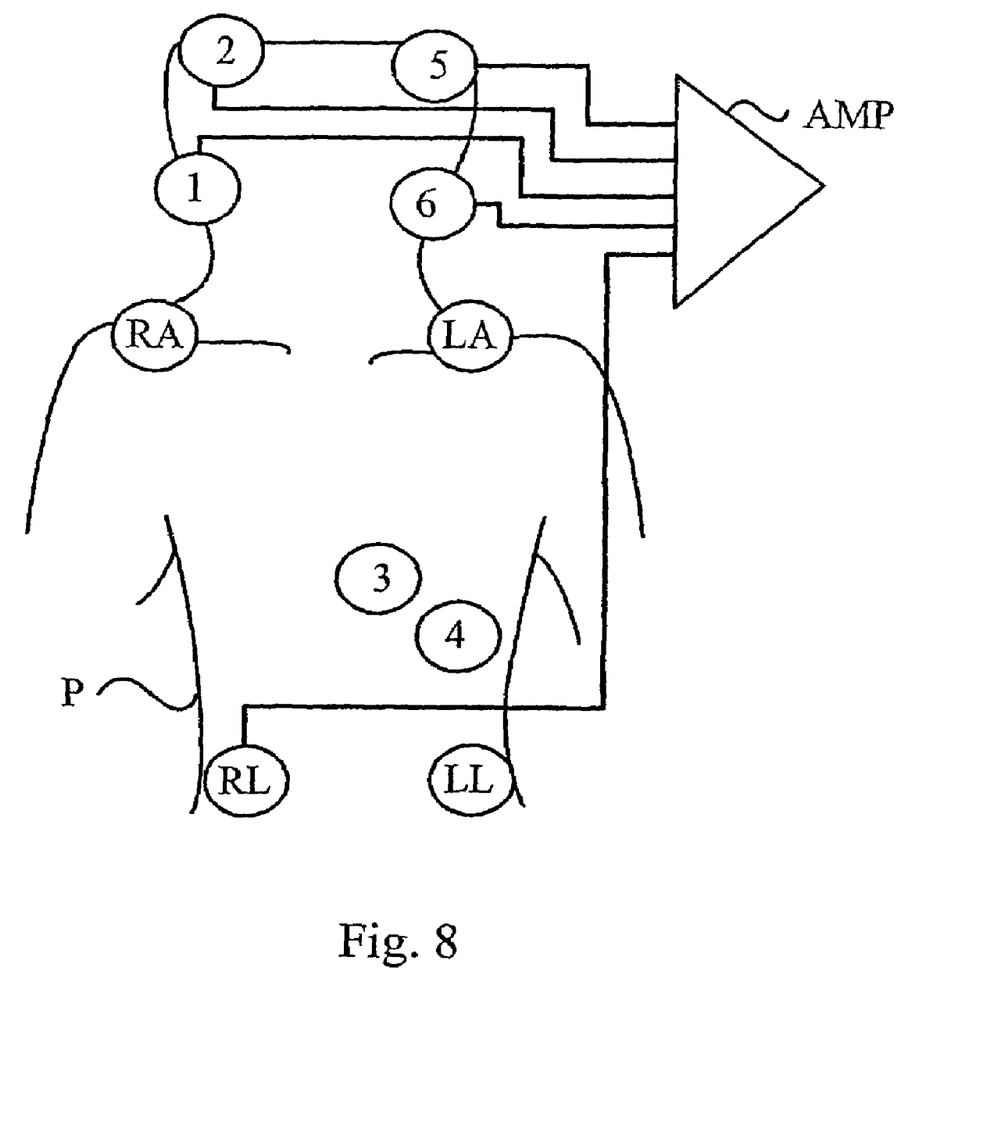
FIG. 8 represents a placement of the electrodes and conductors in accordance with the invention.

FIG. 8 represents one placement of electrodes and conductors in accordance with the invention. The switching of the figure may be used for the measuring of a 5-switched EKG. Connected to the amplifier AMP are the measuring electrodes $V_1$, $V_2$, $V_5$, $V_6$, and RL.

The invention is not restricted merely to the examples of its embodiments referred to above, instead many variations are possible within the scope of the inventive idea defined by the claims.

The invention claimed is:

1. A method for medical monitoring of a patient to obtain a plurality of different physiological signal data from a common electrode set, said common electrode set having four extremity electrodes and up to six additional electrodes, wherein said method comprises the steps of:
    attaching selected electrodes of the common set to the patient in a manner to obtain up to 5 lead EKG signal data using an electrode selection made from the extremity electrodes and at least one additional electrode;
    attaching at least one of the remaining additional electrodes of the common set to the patient in a manner suitable for obtaining EEG signal data or IKG signal data, the attachment of the common electrode set to the patient simultaneously generating a plurality of different physiological and signal data in the common electrode set, the electrodes of the common set being connected to a selection switch (K);
    operating the selection switch (K) for selecting one of: the selected electrodes of the common set or the remaining additional electrodes of the common set; and
    obtaining from the physiological signal data in the electrodes selected by operating the selection switch, one of up to 5 lead EKG signal data or one of EEG and IKG signal data.

2. The method according to claim 1 further comprising the steps of:
    attaching the remaining, additional electrodes to the patient in a manner suitable for obtaining EEG signal data; and
    operating the selector switch (K) to select the remaining additional electrodes;
    and obtaining EEG signal data from the remaining additional electrodes.

3. The method according to claim 1 further comprising the steps of:
    attaching the remaining, additional electrodes to the patient in a manner suitable for obtaining IKG signal data; and
    operating the selector switch (K) to select the remaining additional electrodes;
    and obtaining IKG signal data from the remaining additional electrodes.

4. The method according to claim 1 further comprising the steps of:
    attaching at least one remaining, additional electrode to the patient in a manner to obtain EEG signal data from the patient;
    attaching at least one further remaining additional electrode to the patient in a manner to obtain EMG signal data from the facial region of the patient; and
    obtaining EEG and EMG signal data from the electrodes attached to the patient.

5. The method according to claim 1 further comprising the steps of:
    attaching remaining, additional electrodes to the patient in a manner to obtain EEG signal data; and
    calculating, from the obtained EEG signal data, an index describing a depth of the anesthesia of the patient.

6. The method according to claim 1 wherein EEG signal data is obtained and the electrodes used to obtain EKG signal data and the electrodes used to obtain EEG signal data include a common neutral electrode.

7. The method according to claim 1 further comprising the steps of:
    determining impedance relations among the electrodes; and
    ascertaining from the impedance relations the locations on the patient at which additional remaining electrodes are attached.

8. A system for medical monitoring apparatus comprising:
    a common electrode set including four patient extremity electrodes adapted to be attached to a patient (P) and up to six additional electrodes adapted to be attached to the patient (P), one of said additional electrodes being includable with said extremity electrodes in a first electrode set for obtaining EKG signal data and the remaining additional electrodes being includable in a second electrode set for obtaining EEG or IKG signal data;
    signal conductors connected to each of said electrodes in the common electrode set;
    a common measurement device comprising electrocardiographic (EKG) measuring equipment, electroencephalographic (EEG) measuring equipment and impedance cardiographic (IKG) measuring equipment; and
    a selector switch (K) interposed between said conductors connected to the common electrode set and said measurement device for selecting the measuring equipment to receive physiological data from the first or second electrode set such that when the selector switch (K) is in a first position EKG signal data from the first electrode set is sent to the electrocardiographic measuring equipment, when the selector switch (K) is in a second position the additional electrodes provide a selected one of EEG signal data from the second electrode set that is sent to said electroencephalographic (EEG) measuring equipment and when the selector switch (K) is in a third position IKG signal data from the second electrode set is sent to said impedance cardiographic (IKG) measuring equipment.

9. The system according to claim 8 further comprising:
preamplifier means coupled to said additional electrodes, said preamplifier means having means coupled to selected ones of said additional electrodes for use in obtaining IKG signal data when said switch means is operated to obtain IKG signal data.

10. The system according to claim 8 further comprising:
preamplifier means coupled to said additional electrodes for determining impedance relations among the electrodes for use in ascertaining the locations on the patient at which the electrodes are attached to the patient.

* * * * *